United States Patent
Styrc

(10) Patent No.: US 10,058,423 B2
(45) Date of Patent: Aug. 28, 2018

(54) DEVICE FOR PLACING A SEAL AROUND AN IMPLANT IN A BLOOD VESSEL, AND ASSOCIATED TREATMENT KIT

(71) Applicant: CORMOVE, Ivry-le-Temple (FR)

(72) Inventor: Witold Styrc, Kopstal (LU)

(73) Assignee: Cormove, Ivry-le-Temple (FR)

( * ) Notice: Subject to any disclaimer, the term of this patent is extended or adjusted under 35 U.S.C. 154(b) by 189 days.

(21) Appl. No.: 14/435,668

(22) PCT Filed: Oct. 23, 2013

(86) PCT No.: PCT/EP2013/072217
§ 371 (c)(1),
(2) Date: Apr. 14, 2015

(87) PCT Pub. No.: WO2014/064174
PCT Pub. Date: May 1, 2014

(65) Prior Publication Data
US 2015/0351907 A1 Dec. 10, 2015

(30) Foreign Application Priority Data
Oct. 25, 2012 (FR) ...................................... 12 60193

(51) Int. Cl.
*A61F 2/24* (2006.01)
(52) U.S. Cl.
CPC .... *A61F 2/2436* (2013.01); *A61F 2250/0069* (2013.01)
(58) Field of Classification Search
CPC ... A61F 2/24; A61F 2/2436; A61F 2250/0069
See application file for complete search history.

(56) References Cited

U.S. PATENT DOCUMENTS

| 2004/0210304 A1 | 10/2004 | Seguin et al. |
| 2005/0283231 A1* | 12/2005 | Haug ............ A61F 2/2418 623/2.11 |
| 2008/0077234 A1 | 3/2008 | Styrc |
| 2009/0299449 A1 | 12/2009 | Styrc |
| 2010/0280589 A1 | 11/2010 | Styrc |

FOREIGN PATENT DOCUMENTS

| FR | 2 874 813 | 3/2006 |
| WO | WO 2006/027499 | 3/2006 |
| WO | WO 2006/089236 | 8/2006 |
| WO | WO2006/123046 | 11/2006 |
| WO | WO 2009/044082 | 4/2009 |
| WO | WO 2011/106547 | 9/2011 |
| WO | WO 2014/056754 | 4/2014 |

* cited by examiner

*Primary Examiner* — Victor Nguyen
(74) *Attorney, Agent, or Firm* — Davidson, Davidson & Kappel, LLC

(57) ABSTRACT

A device for placing a seal around an implant in a blood vessel, and associated treatment kit are provided. This device (24) includes a hollow sheath (60) having a longitudinal axis (Y-Y'), and at least one release member (62), which may be deployed with respect to the sheath (60) between a retracted position in the sheath (60) and an extracted position out of the sheath (60). The device (24) includes, for said or each release member (62), a seal body (64) having an angular extent strictly less than 360° around the longitudinal axis (Y-Y'), the seal body (64) being releasably attached onto the release member (62) so as to be released from the release member (62).

21 Claims, 4 Drawing Sheets

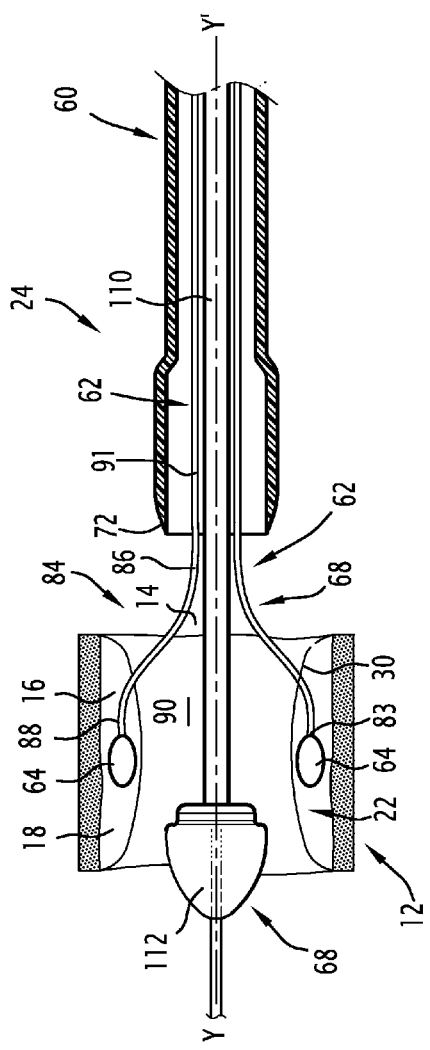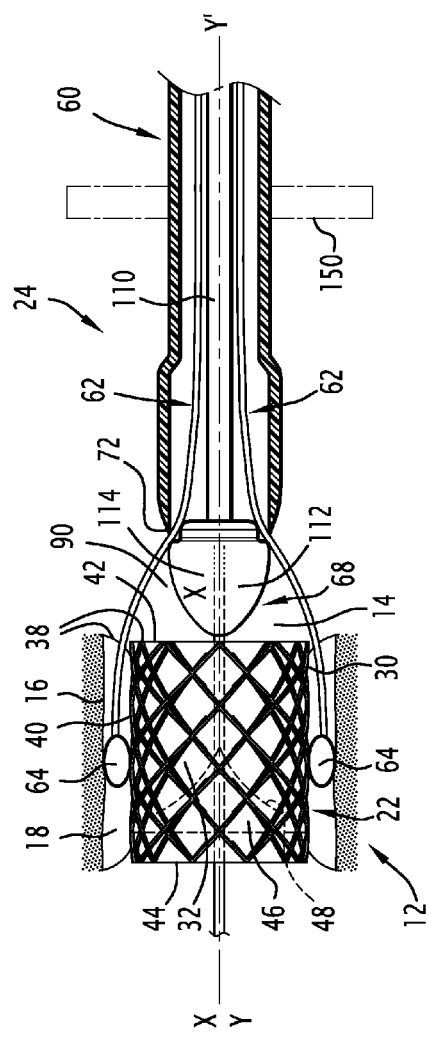

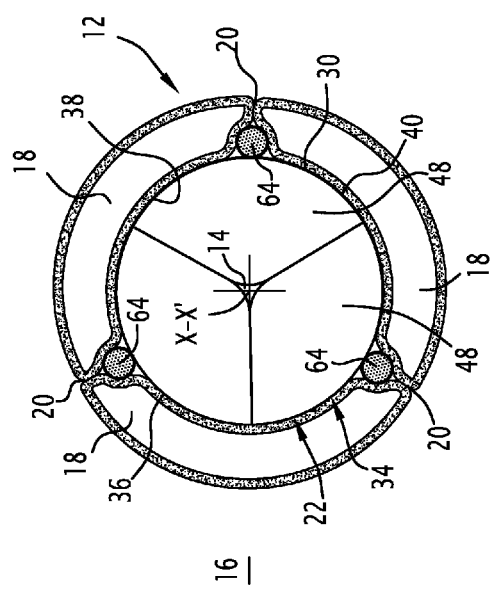

DEVICE FOR PLACING A SEAL AROUND AN IMPLANT IN A BLOOD VESSEL, AND ASSOCIATED TREATMENT KIT

The present invention relates to a device for placing a seal around an implant in a blood vessel, comprising:

a hollow sheath having a longitudinal axis;

at least one release member, which may be deployed with respect to the sheath between a retracted position in the sheath and an extracted position out of the sheath.

This device is notably applied to the treatment of cardiac valves.

The heart includes valves which are present at the outlet of the right ventricle (pulmonary and tricuspid valve) and of the left ventricle (aortic and mitral valve).

These valves ensure a unique circulation of the blood flow, avoiding blood backflow at the end of the ventricular contraction.

BACKGROUND

However, diseases or malformations affect proper operation of the valves.

In particular, the latter may suffer from calcification thus allowing backflow or regurgitation into the ventricle or atrium having expelled the blood flow. The regurgitation problem leads to abnormal expansion of the ventricle which finally produces heart failure. In certain cases, the valve comprises a number of leaflets smaller than the one generally observed for this type of valve, which may be detrimental to its operation in the long run.

In order to treat this type of disease in a surgical way, implantation of an endovalve between the leaflets of the affected native valve is known. This endovalve comprises a tubular endoprosthesis formed by a self-extensible trellis and a flexible obturator or valve most often made in a tissue of animal origin. The flexible obturator is permanently fixed in the endoprosthesis.

Such endovalves are implantable via an endolumen route, which considerably limits the risks associated with the implantation of the valve, notably in terms of mortality.

In certain cases, the endovalves do not give entire satisfaction after their implantation. Indeed, although the outer surface of the endoprosthesis is spontaneously applied against the seat of the native valve, flattening the leaflets between the seat and the outer surface of the endoprosthesis, leaks may subsist around the outer surface of the endoprosthesis, notably at the commissures defined between the leaflets of the native valve. These leaks occur in more than 50% of the patients having been subject to such an operation.

In order to overcome this problem, US 2005/0283231 describes an implant comprising an endoprosthesis and a prosthetic valve fixed in the endoprosthesis. The leaflets of the prosthetic valve of the endoprosthesis are extended with foldable segments around the endoprosthesis so as to be interposed between the wall of the conduit and the outer surface of the endoprosthesis. These folded segments around the endoprosthesis are able to at least partly fill the leaks which may occur around the valve.

SUMMARY OF THE INVENTION

However, each segment is bound to the valve. It is therefore difficult to position it accurately, in particular with respect to the endoprosthesis and/or to the blood flow conduit in which the implant is placed. In particular, the position in which the folded segment has to be placed in the native valve is difficult to determine in order to ensure a good seal around the endoprosthesis.

Further, the exact position of the commissures defined by a native valve varies from one patient to the other. The foldable segments are therefore not necessarily adapted to the particular morphology of certain patients.

An object of the invention is to provide a treatment device comprising an implant which may be sealably implanted in a blood vessel, the seal being easily made and in an adaptable way to the anatomic configuration of the patient.

A device of the aforementioned type is provided, characterized in that the device comprises, for said or each release member, a seal body having an angular extent strictly less than 360° around the longitudinal axis, the seal body being attached so as to be releasable on the release member so as to be released from the release member.

The device according to the invention may comprise one or more of the following features, taken individually or according to all technically possible combinations:

it comprises a plurality of release members angularly spaced out relatively to each other around the longitudinal axis, each release member bearing a seal body releasably attached on the release member so as to be released from the release member;

it comprises a releasable retaining member of said or each seal body on the release member, the releasable retaining member being displaceable with respect to the seal body between a configuration engaged with the seal body and a configuration for releasing the seal body;

the release member delimits an internal channel, the releasable retaining member being positioned at least partly in the internal channel;

in the extracted position, said or each release member has a flared distal portion protruding transversely beyond the sheath, the flared distal portion advantageously having a first segment moving away from the longitudinal axis and a second segment parallel to the longitudinal axis or moving closer to the longitudinal axis;

it includes an assembly for closing the sheath comprising a central support positioned at least partly in the sheath and a nose mounted to the distal end of the central support, said or each release member being at least partly positioned between the sheath and the central support;

it includes an assembly for closing the sheath comprising a central support at least partly positioned in the sheath and a nose mounted at the distal end of the central support, said or each release member being at least partly positioned positioned between the sheath and the central support;

the closure assembly is movable between a proximal position for obturating the sheath and a distal position for opening the sheath, wherein said or each release member is able to pass from its contracted position to its expanded position;

the closure assembly is movable from the distal position, when said or each release member occupies its extracted position, towards an intermediate transverse separation position of said or each seal body, in which the nose cooperates with said or each release member for transversely moving it away from the longitudinal axis;

it includes at least one system for transversely moving away the release member, able to be interposed between the nose and the release member in the intermediate separation position;

each release member is slidably mounted on the support;

said or each seal body includes a block in a flexible material advantageously in foam, and a stiff central framework, positioned in the block in flexible material.

the sheath does not contain any implant intended to be implanted in a blood vessel between said or each seal body.

The subject-matter of the invention also includes a kit for treating a blood vessel, comprising:

an implant intended to be implanted in a blood vessel;
a device as described above, said or each seal body being intended to be placed around the implant in the blood vessel.

The kit according to the invention may comprise one or more of the following features, taken individually or according to any technically possible combination:

the implant includes an endoprosthesis which may be deployed between a contracted state and an expanded state, the endoprosthesis advantageously bearing a valve;

it includes a tool for releasing the implant, able to be introduced into the blood vessel, independently of the device for setting it into place.

The subject-matter of the invention also includes a method for treating a blood vessel comprising the following steps:

introducing a device as defined above in a blood vessel;
deploying said or each release member in its extracted position;
releasing said or each seal body from the release member;
withdrawing said or each release member and the sheath out of the blood vessel.

The method according to the invention may comprise, between the deployment step and the release step, the following steps:

introducing an implant in a retracted state between said or each release member;
radially expanding the implant toward its deployed state, said or each seal body being interposed between the implant and a body surface defining the blood vessel passage.

BRIEF DESCRIPTION OF THE DRAWINGS

The invention will be better understood upon reading the description which follows, only given as an example and made with reference to the appended drawings, wherein:

FIG. 5 is a view similar to FIG. 1, during a first step for producing the seal around an implant;

FIG. 6 is a view similar to FIG. 1, during a second step for producing the seal around an implant;

FIG. 7 is a sectional view taken along a transverse plane, of a blood vessel in which is implanted an implant and a plurality of seal bodies having been released by the device according to the invention;

FIG. 8 is a view similar to FIG. 5 of a second device for placing a seal according to the invention.

DETAILED DESCRIPTION

Figure 1:
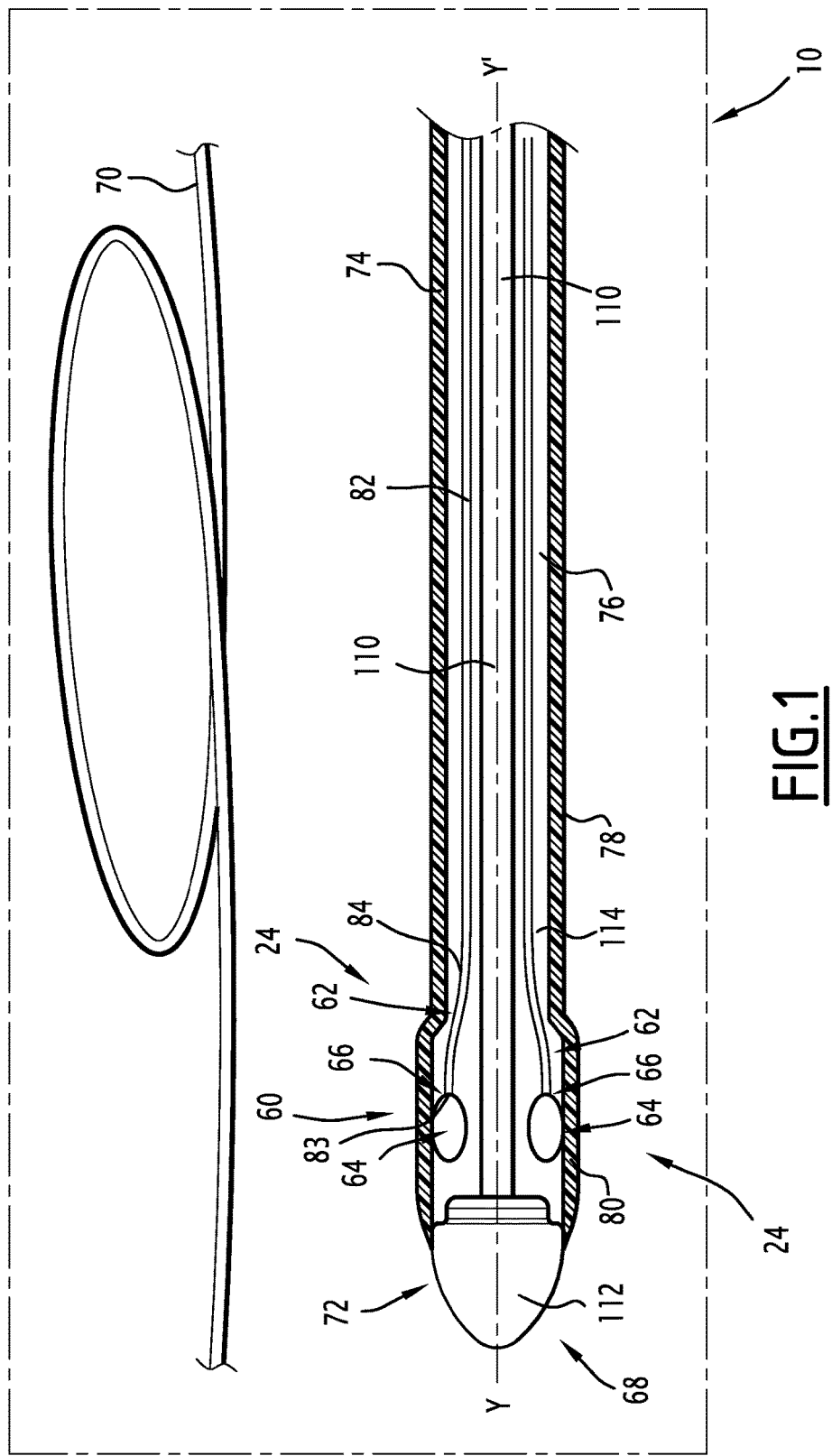
FIG. 1 is a schematic partial sectional view of a treatment kit comprising a first device for placing a seal according to the invention.

A first treatment kit 10 for blood according to an embodiment of the invention is illustrated in FIGS. 1 to 6.

This kit 10 is in particular intended for implanting an endovalve comprising a tubular endoprosthesis and a valve, as a replacement of a native cardiac valve 12, partly visible in FIGS. 6 and 7.

As illustrated in FIGS. 6 and 7, the native valve 12 is located in a blood vessel 14 delimited inside a peripheral wall 16. The native valve 12 comprises a plurality of movable native leaflets 18 in the passage 14 from the wall 16.

The native valve 12 illustrated as an example in FIG. 7 includes three native leaflets 18.

The native valve 12 delimits, between each pair of native leaflets 18, a commissure 20 located at the junction between the native leaflets 18 at the wall 16.

The kit 10 further comprises an implant 22, visible in FIGS. 6 and 7, intended to be placed in the blood flow passage 14, and a tool for releasing the implant 22 in the passage 14.

According to this embodiment of the invention, the kit 10 further includes a device 24 for placing a seal in the intermediate space located between the implant 22 and the peripheral wall 16, around the implant 22.

With reference to FIG. 6, the implant 22 includes an endoprosthesis 30, which advantageously forms an endovalve.

The endoprosthesis 30 has a tubular shape with an axis X-X'. It delimits a central passage 32 for blood flow axially opening onto either side of the endoprosthesis 30. The endoprosthesis 30 bears a valve 34 or obturator added on the endoprosthesis 30 inside the passage 32.

The endoprosthesis 30 is formed by an openworked tubular framework 36 comprising a trellis of wires which have spring properties. The framework 36 is obtained by braiding at least one stainless steel wire, of a shape memory alloy, or of a polymer. Alternatively, the framework 36 is obtained by cutting a tube, for example by means of a laser.

With reference to FIG. 7, the framework 36 defines an inner peripheral surface 38 and an outer peripheral surface 40. The surfaces 38 and 40 are substantially cylindrical and extend around the axis X-X' between a proximal peripheral edge 42, located on the right in FIG. 6 and a distal peripheral edge 44, located on the left in FIG. 6.

The inner surface 38 interiorly defines the central passage 32. The outer surface 40 is intended to be at least partly flattened against the wall 16 and/or against the leaflets 18, as this will be seen later on.

The framework 36 of the endoprosthesis 30 may be deployed between a contracted state, in which it has a small diameter, with view to its introduction into the conduit 14, and an expanded state, forming its rest state, in which it has a large diameter. In the example illustrated in FIGS. 1 to 4, the framework 36 may be spontaneously deployed between its contracted state and its expanded state. It is thus self-expansible.

The valve 34 is for example made on the basis of a native valve of an animal like a pig. Alternatively, it is made on the basis of natural tissues like bovine, ovine or porcine pericardium, or based on synthetic tissues.

Conventionally, the valve 34 comprises a tubular base 46 attached on the inner surface 38 of the framework 36, and several flexible leaflets 48 for obturating the central passage 32 which extend the base 46 downwards.

The leaflets 48 may be radially displaced towards the axis X-X' of the passage 38 between an obturation position, in which they substantially and totally prevent passing of blood through the passage 32, and a position for clearing the passage 32 in which they are substantially flattened against the inner surface 38 and let blood through the passage 32.

In the obturation position, the leaflets 48 have a section which converges towards the proximal edge 42 of the valve.

The release tool is for example the release tool described in FR-A-2 863 160, which is also published as U.S. Pub. 2005/0119722, which is incorporated by reference herein, more specifically the release tool of which is hereby incorporated by reference herein. It is able to maintain the framework 36 in its contracted state upon its introduction into the blood vessel passage 14, and then deploy the framework 36 in its expanded state at its point of introduction, advantageously placed in the native valve 12.

With reference to FIGS. 1 to 6, the placing device 24 includes a confinement and transport sheath 60, and at least one release member 62, movably mounted in the sheath 60 between a retracted position in the sheath 60, visible in FIG. 1, and an extracted position out of the sheath 60, visible in FIGS. 5 and 6.

The placing device 24 further includes, for each release member 62, a seal body 64 intended to be interposed between the implant 22 and the wall 16, and an attachment assembly 66 releasable from the seal body 64 on the release member 62.

The placing device 24 advantageously includes an assembly 68 for closing the sheath 60 and a surgical guide 70 for introducing and guiding the device 24 in the passage 14.

The confinement sheath 60 extends along a longitudinal axis Y-Y' between a proximal end intended to be located out of the body of the patient, and a distal end 72, intended to be introduced into the blood flow passage 14 as far as the point of implantation of the implant 22.

The sheath 60 is for example formed by a hollow tube 74 in a flexible material. It delimits a central lumen 76 opening at the proximal end (not visible), intended to be placed out of the body of the patient and at the distal end 72, intended to be inserted into the passage 14.

In the example illustrated in FIG. 1, the sheath 60 includes a tubular proximal portion 78 and a distal capsule 80 with a transverse extent greater than the transverse extent of the proximal portion 78.

The capsule 80 receives each seal body 64 into the retraction position of the release member 62.

In this example, the placing device 24 includes a plurality of independent release members 62 each bearing a seal body 64.

The number of release members 62 is for example comprised between 1 and 4. The release members 62 are positioned at least partly in the internal lumen 76 of the sheath 60 by being spaced apart angularly from each other.

Each release member 62 includes a rod 82 extending between a proximal end able to be extracted out of the sheath 60 so as to be manoeuvred by a user of the device out of the body of the patient, and a distal end 83 on which is attached the seal body 64.

The rod 82 is self-supporting in order to allow a user of the device to push the seal body 64 out of the sheath 60 in the passage 14, during displacement of the release member 62 from its retracted position to its extracted position.

The release member 62 has a spontaneously deformable distal portion 84 from a configuration radially contracted towards the axis Y-Y' which it occupies in the retracted position (see FIG. 1) and a radially deployed configuration away from the axis Y-Y', which it occupies in the extracted position (see FIG. 5).

In the deployed configuration, the distal portion 84 is transversely flared. It has a proximal segment 86 moving away from the axis Y-Y' and a distal segment 88 parallel to the axis Y-Y', or moving closer to the axis Y-Y'.

The distal portions 84 of the different release members 62 thus delimit between them a central space 90 for inserting the implant 12, facilitating the placing of the implant 12.

As illustrated by FIGS. 1 and 5, each release member 62 may be moved by sliding along the axis Y-Y' between the retracted position, visible in FIG. 1, and the extracted position, visible in FIG. 5.

In the retracted position, the distal portion 84 of the release member 62 and the seal body 64 attached on the release member 62 are totally received in the sheath 60, advantageously at the capsule 80.

The sheath 60 thus maintains the distal portion 84 in its contracted configuration.

In the extracted position, the distal portion 84 and the seal body 64 have been pushed distally out of the sheath 60, beyond the distal end 72. The distal portion 84 occupies its radially deployed configuration.

Figure 2:
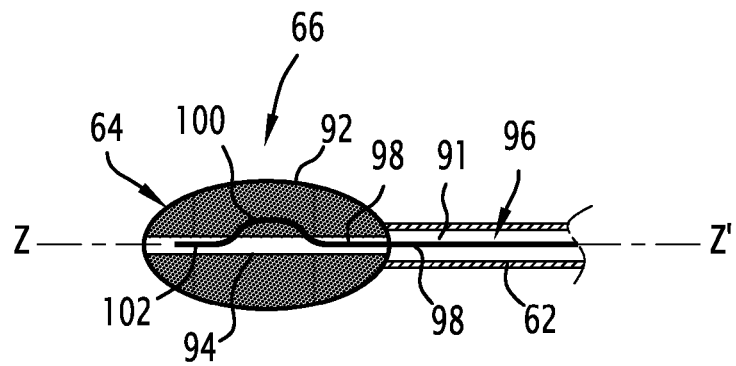
FIG. 2 is a view of a detail of the device of FIG. 1, illustrating a first alternative of a seal body intended to be placed around an implant.

In the example illustrated in FIGS. 1 and 2, the rod 82 forming the release member 62 is hollow. It delimits an internal flow channel 92 of the releasable attachment assembly 66.

With reference to FIGS. 2 and 7, each seal body 64 has an angular extent around the axis Y-Y' of less than 360°, advantageously less than 180°, still advantageously less than 45°.

Each seal body 64 thus forms a point like cushion.

With reference to FIG. 2, each seal body 64 is elongated along an elongation axis Z-Z'. It advantageously has an olive shape.

In the example of FIG. 2, the seal body 64 includes a block 92 of deformable material and a stiff central framework 94 positioned in the block 92.

The block 92 is for example formed on the basis of foam, notably silicone or polymethane foam. Alternatively, it is formed with discrete fabric elements housed in an outer cover.

In the example of FIG. 2, the framework 94 includes a hollow central tubular rib with an axis Z-Z', around which the block 92 is positioned.

The framework 94 is formed on the basis of a stiffer material than the material forming the block 92.

Thus, the seal body 64 is able to be deformed when it is inserted between the implant 22 and the peripheral wall 16 so as to fit the shape of the intermediate space between the implant 22 and the peripheral wall 16.

The seal body 64 is releasably attached on the distal portion 84 of the release member 62, advantageously end-to-end with the distal end 83.

Its elongation axis Z-Z' thus forms a small or zero angle, advantageously less than 30°, with respect to the local axis of the distal portion 84 at the point of contact with the seal body 64.

The releasable attachment assembly 66 includes in this example a retention member 96 movable in the internal channel 91 and through the seal body 64, between a configuration of engagement with the seal body 64, and a configuration for releasing the seal body 64.

In this example, the retaining member 96 is formed by a pin, which advantageously extends over the whole length of the release member 62. The retaining member 96 is thus able to be handled by an operator of the device 24 out of the body of the patient in order to pass from its engagement configuration to its release configuration.

In the engagement configuration, visible in FIG. 2, the retaining member 96 is engaged through the seal body 64.

In the particular example illustrated in FIG. 2, the retaining member 96 includes, in the vicinity of its distal end, a proximal free segment 98 positioned in the channel 92 and in the framework 94, and a radially deformed convex segment 100 which penetrates into the block 92 of deformable material. It advantageously includes a distal free segment 102.

In the release configuration, the radially deformed segment 100 and the distal free segment 102 have been extracted out of the seal body 64.

As illustrated by FIGS. 1, 5, and 6, the closure assembly 68 includes a support 110 inserted into the sheath 60, and a distal nose 112 intended to obturate the sheath 60.

The support 110 is positioned in the sheath 60 substantially at the centre of the latter. It delimits, in the internal volume 76, an annular space 114 receiving each release member 62.

The nose 112 has a maximum transverse extent greater than or equal to the maximum transverse extent of the sheath 60, at the distal end 72. It has a profiled distal portion for facilitating its insertion into the blood vessel 14.

The support 110 and the nose 112 interiorly delimit an axial through-passage 114, partly illustrated in FIG. 6, for receiving the surgical guide 70.

The closure assembly 68 is movable between a proximal position for obturating the sheath 60, visible in FIG. 1, and a distal position for opening the sheath 60, visible in FIG. 5.

In the proximal position, the nose 112 is placed in contact with the distal end 72 of the sheath 60 for obturating the internal lumen 76. Advantageously, a proximal portion of the nose 112 is inserted into the internal lumen 76, and the distal portion of the nose 112 protrudes out of the lumen 76.

The nose 112 thus prevents passing of each release member 62 from the retracted position to the extracted position.

In the distal position, the nose 112 is positioned axially away from the distal end 72. The support 110 is partly extracted out of the internal lumen 76 through the distal end 72.

The internal lumen 76 opens at the distal end 72 and passing of each release member 62 from the retracted position to the extracted position is possible.

Further, when the closure assembly 68 occupies its distal position, and each release member 62 occupies its extracted position, the closure assembly 68 is displaceable towards transverse separation intermediate position of each seal body 64, visible in FIG. 6.

In this position, the nose 112 is brought closer to the distal end 72 of the sheath 60. It cooperates with each release member 62 for displacing it transversely away from the longitudinal axis Y-Y'. This radially moves away each seal body 64.

The operation of the treatment kit 10 according to an embodiment of the invention will now be described.

Initially, a kit 10 is provided to the practitioner. The placing device 24 is then configured so that each release member 62 occupies its retracted position in the confinement sheath 60 as illustrated by FIG. 1.

Each seal body 64 is then attached to the end of a release member 62 by the releasable attachment assembly 66. Each seal body 64 is received in the inner volume 76 of the sheath 60, advantageously at the capsule 80.

The closure assembly 68 then occupies its proximal position for obturating the sheath 60. The support 110 is positioned between the release members 62, in the centre of the sheath 60. The nose 112 obturates the distal end 72 of the sheath 60.

The practitioner then grasps the guide 70 and introduces it via an endoluminal route into the blood system as far as an implantation point provided in a blood vessel 14.

When the implant 22 is an endovalve, the point of implantation is for example located facing a native valve 12.

Next, the practitioner slips the placing device 24 onto the surgical guide 70 and brings the device 24 as far as the implantation point by sliding on the guide 70.

Subsequently, the practitioner passes the closure assembly 68 from its proximal position to its distal position, in order to open the sheath 60 at the distal end 72.

The practitioner then extracts each release member 62 bearing a seal body 64 out of the sheath 60. In the extracted position, the distal portion 84 of each release member 62 passes from its radially contracted configuration to its radially deployed configuration.

During this passing, each seal body 64 is brought closer to the wall 16 delimiting the passage 14 so as to advantageously come into contact with this wall 16.

In the case when the implantation point is located in a native valve 12, the practitioner for example introduces each seal body 64 into a commissure 20 of the valve 12 located between two adjacent native leaflets 18.

Next, the practitioner moves the closure 68 towards the distal end 72 in order to attain the intermediate separation position. The nose 112 then cooperates with each release member 62 in order to cause additional radial separation of the seal member 64 attached on the release member 62.

Further, the central space 90 located between the release member 62 is cleared. The practitioner then introduces an additional surgical guide as far as the central space 90, advantageously through a route opposed to the route for introducing the guide 70.

The practitioner then guides the release tool of the implant 22 on the additional guide and deploys the implant 22 in the central space 90, facing each seal body 64, as illustrated by FIG. 6.

With reference to FIG. 7, the outer peripheral surface 40 of the framework 36 then pushes each seal body 64 radially away from the axis Y-Y' against the wall 16.

Each seal body 64 is therefore interposed between the implant 22 and the peripheral wall 16 in the blood vessel passage 14, so as to substantially block the intermediate space present between the implant 22 and the wall 16, in particular at the commissures 20 of the native valve 12.

Next, the practitioner releases each seal body 64 from the release member 62 on which it is attached. For this purpose, he/she displaces the retaining member 96 from its engagement configuration with the seal body 64 towards the release configuration, by maintaining the seal body 64 substantially in position bearing upon the release member 62.

The practitioner then retracts each release member 62 in the sheath 60, and then proceeds with withdrawal of the sheath 60.

The device 24 therefore gives the possibility of achieving easily and accurately an efficient seal around the implant 22 positioned in a blood vessel passage 14, by adaptation to the conformation of the intermediate space present between the implant 22 and the peripheral wall 16 delimiting the passage 14.

Figure 3:
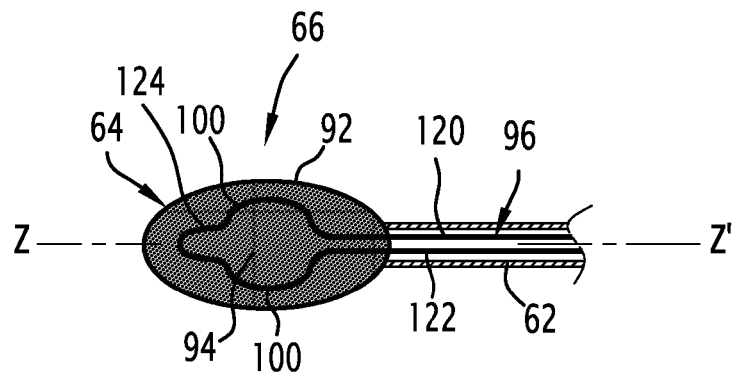
FIG. 3 is a view similar to FIG. 2, illustrating a second alternative of a seal body.

In an embodiment illustrated by FIG. 3, the seal body 64 is formed with a block 92 without any central framework 94. The retaining member 96 includes two parallel strands 120, 122 folded back as a loop 124 at the distal end of the retaining member 96 introduced into the block 92. The loop 124 includes two opposite deformed segments 100, transversely protruding with respect to the Z-Z' axis.

The release of the seal body 64 illustrated in FIG. 3 is carried out in a similar way to that described for the body 64 of FIG. 2, by pulling on the strands 120, 122 of the retaining member 96 positioned in the channel 91.

Figure 4:
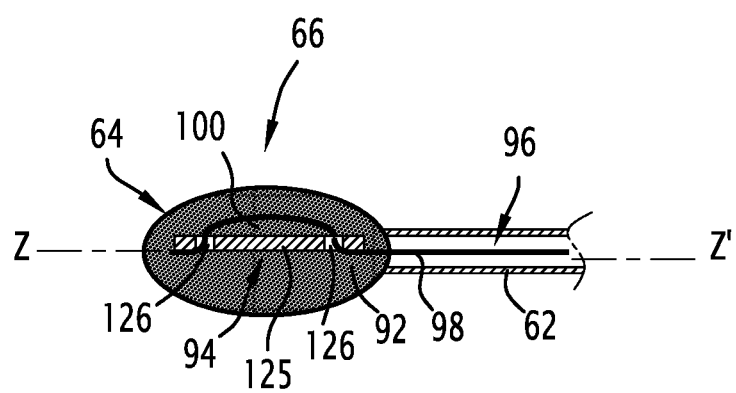
FIG. 4 is a view similar to FIG. 2, illustrating a third alternative of a seal body.

In another alternative illustrated by FIG. 4, the central framework 94 is formed by a substantially flat member, such as an elongated disc 125. The disc 125 is provided with eyelets 126 providing the passage for the retaining member 96.

The release of the seal body 64 illustrated in FIG. 4 is carried out in a similar way to the one described for the body 64 of FIG. 2.

In an alternative illustrated in dotted lines in FIG. 6, the device 24 includes a filter 150 which may be transversely deployed around the sheath 60. The filter 150 is deployed during the setting into place of each seal body 64 for recovering possible released calcification debris from native leaflets 18.

The device 24 for setting into place a second kit 130 according to an embodiment of the invention is illustrated by FIG. 8.

Unlike the device 24 illustrated in FIGS. 1 to 6, the device 24 includes a common member 132 for simultaneous maneuvering of the release member 62.

In this example, the common maneuvering member 132 is formed by a sleeve slidably mounted around the support 110 along the axis Y-Y'.

Each release member 62 has a proximal end 134 positioned in the lumen 76 of the sheath 60. The proximal end 134 is attached on the common maneuvering member 132, advantageously at its distal end, for example with a collar 136.

The device 24 further preferably includes a system 138 for radial separation of each seal body 64, interposed between the closure assembly 68 and each release member 62.

The separation system 138 for example includes a tab 140 attached on one of the release members 62 or of the closure assembly 68, the tab 140 having a free end 142 able to cooperate with the other one of the release members 62 and of the closure assembly 68.

In the example illustrated in FIG. 8, the tab 140 is attached onto the release member 62 and has a free end 142 protruding in the central space 90 facing the support 110.

The operation of the second kit 130 differs from the operation of the first kit 10 in that, after passing of the closure assembly 68 into its distal position for opening the sheath 60, the common maneuvering member 132 is distally displaced along the support 110. The release members 62 are simultaneously deployed towards their extracted position by actuation of the common member 132.

Next, upon return of the closure assembly 68 to the intermediate position, the nose 112 comes into contact with the free end 142 of each tab 140, causing a radial separation of the release member 62 and of the seal body 64 attached onto the release member 62.

The operation of the second kit 130 is moreover similar to that of the first kit 10.

The invention claimed is:

1. A device for setting into place a seal around an implant in a blood vessel passage comprising:
   a hollow sheath having a longitudinal axis;
   at least one releaser configured to be deployed with respect to the sheath between a retracted position in the sheath and an extracted position out of the sheath; and
   a seal body having an angular extent of strictly less than 360° around the longitudinal axis, the seal body being releasably attached onto the releaser so as to be released from the releaser, wherein the or each seal body includes a block in a flexible material and a stiff central framework positioned in the block in flexible material.

2. The device as recited in claim 1 comprising a plurality of releasers spaced apart angularly from each other around the longitudinal axis, each releaser bearing a seal body releasably attached onto the releaser so as to be released from the releaser.

3. The device as recited in claim 1 comprising a releasable retaining member of the or each seal body on the releaser, the releasable retaining member being displaceable with respect to the seal body between a configuration of engagement with the seal body and a configuration for release from the seal body.

4. The device as recited in claim 3 wherein the releaser delimits an internal channel, the releasable retaining member being at least partly positioned in the internal channel.

5. The device as recited in claim 1 wherein, in the extracted position, the or each releaser has a flared distal portion transversely protruding beyond the sheath.

6. The device as recited in claim 5 wherein the flared distal portion has a first segment extending away from the longitudinal axis and a second segment parallel to the longitudinal axis or extending closer to the longitudinal axis.

7. The device as recited in claim 1 comprising a closure assembly for closing the sheath comprising a central support positioned at least partly in the sheath and a nose mounted at the distal end of the central support, the or each releaser being at least partly positioned between the sheath and the central support.

8. The device as recited in claim 7 wherein the closure assembly is movable between a proximal position for obturating the sheath and a distal position for opening the sheath, in which the or each releaser is configured to pass from its retracted position to its extracted position.

9. The device as recited in claim 8 wherein the closure assembly is movable from the distal position, when the or each releaser occupies its extracted position, to a transverse separation intermediate position of the or each seal body, in which the nose cooperates with the or each releaser for displacing it transversely away from the longitudinal axis.

10. The device as recited in claim 9 including at least one system for transverse separation of the releaser, able to be interposed between the nose and the releaser in the intermediate separation position.

11. The device as recited in claim 7 wherein the or each releaser is slidably mounted on the support.

12. The device as recited in claim 1 wherein the block is foam.

13. A treatment kit for a blood vessel passage comprising:
    an implant intended to be implanted in a blood vessel passage;
    the device as recited in claim 1, the or each seal body being intended to be positioned around the implant in the blood vessel passage.

14. The kit as recited in claim 13 wherein the implant includes an endoprosthesis deployable between a contracted state and an expanded state, the endoprosthesis advantageously bearing a valve.

15. The kit as recited in claim 14 wherein the endoprosthesis bears a valve.

16. The kit as recited in claim 13 further comprising a release tool for releasing the implant, the release tool being able to be introduced into the blood vessel passage independently of the device.

17. A method for treating a blood vessel comprising the following steps:
- introducing the device as recited in claim 1 in a blood vessel;
- deploying the or each releaser in the extracted position;
- releasing the or each seal body from the releaser; and
- withdrawing the or each releaser and the sheath out of the blood vessel.

18. The method as recited in claim 17 comprising, between the deployment step and the release step, the following steps:
- introducing an implant in a retracted state between the or each releaser;
- radially expanding the implant toward a deployed state, the or each seal body being interposed between the implant and a body surface defining the blood vessel passage.

19. A device for setting into place a seal around an implant in a blood vessel passage comprising:
- a hollow sheath having a longitudinal axis;
- at least one releaser configured to be deployed with respect to the sheath between a retracted position in the sheath and an extracted position out of the sheath; and
- a seal body having an angular extent of strictly less than 360° around the longitudinal axis, the seal body being releasably attached onto the releaser so as to be released from the releaser, wherein the or each seal body has an elongated shape along an elongation axis, notably an olive shape.

20. A treatment kit for a blood vessel passage comprising:
- an implant intended to be implanted in a blood vessel passage;
- the device as recited in claim 19, the or each seal body being intended to be positioned around the implant in the blood vessel passage.

21. A method for treating a blood vessel comprising the following steps:
- introducing the device as recited in claim 19 in a blood vessel;
- deploying the or each releaser in the extracted position;
- releasing the or each seal body from the releaser; and
- withdrawing the or each releaser and the sheath out of the blood vessel.

\* \* \* \* \*